United States Patent
Bublewitz et al.

(10) Patent No.: US 6,566,479 B1
(45) Date of Patent: May 20, 2003

(54) RELINING FOR PROSTHESES AND PROCESS THE MANUFACTURING THEREOF

(75) Inventors: Alexander Bublewitz, Herborn (DE); Jens-Peter Reber, Herborn (DE)

(73) Assignee: Kettenbach GmbH & Co. KG, Eschenburg (DE)

(*) Notice: Subject to any disclaimer, the term of this patent is extended or adjusted under 35 U.S.C. 154(b) by 0 days.

(21) Appl. No.: 09/600,920

(22) PCT Filed: Mar. 26, 1998

(86) PCT No.: PCT/EP98/01457

§ 371 (c)(1), (2), (4) Date: Feb. 2, 2001

(87) PCT Pub. No.: WO99/37272

PCT Pub. Date: Jul. 29, 1999

(30) Foreign Application Priority Data

Jan. 22, 1998 (DE) .................................... 298 00 814 U

(51) Int. Cl.⁷ .............................................. C08G 77/06
(52) U.S. Cl. ............................. 528/15; 528/15; 528/31; 523/118; 523/120; 524/588; 526/279
(58) Field of Search .......................... 526/279; 523/118, 523/120; 528/31, 15; 524/588

(56) References Cited

U.S. PATENT DOCUMENTS

| 5,151,479 A | * | 9/1992 | Mukai et al. | ............... 526/277 |
|---|---|---|---|---|
| 5,288,827 A | * | 2/1994 | Li et al. | ...................... 526/279 |
| 5,476,912 A | * | 12/1995 | Hosoi et al. | ................. 526/279 |
| 5,575,645 A | * | 11/1996 | Jacobs et al. | ................... 433/9 |
| 5,612,433 A | * | 3/1997 | Ono et al. | .................... 526/279 |
| 6,251,966 B1 | * | 6/2001 | Fry et al. | .................... 523/109 |
| 6,255,407 B1 | * | 7/2001 | Neffgen | ...................... 525/342 |

FOREIGN PATENT DOCUMENTS

| DE | 39 11 520 | | 10/1990 |
|---|---|---|---|
| EP | 0 614 655 | | 9/1994 |
| EP | 0 632 060 | | 1/1995 |
| JP | 2-43209 | * | 2/1990 |
| JP | 4-68007 | * | 3/1992 |
| WO | WO91/17046 | | 11/1991 |

OTHER PUBLICATIONS

Abstract 4–68007, Mar. 1992.*
Abstract 2–43209, Feb. 1990.*
Derwent abstract, JP 07 291820, Nov. 1995.*

* cited by examiner

Primary Examiner—Margaret G. Moore
(74) Attorney, Agent, or Firm—Jacobson Holman PLLC

(57) ABSTRACT

In order to provide a relining for prosthesis and a process for the manufacturing thereof with improving the performance of the relining and the application-technical characteristics of the individual components as compared with the state of the art, it is proposed to prepare the relining from a one-component relining adhesive, a two-component relining silicone and optionally a two-component sealing lacquer.

10 Claims, 1 Drawing Sheet

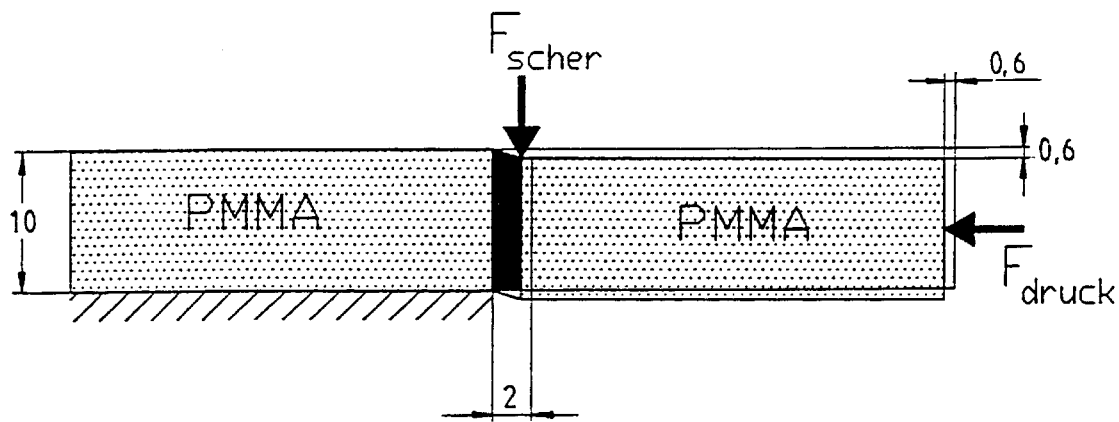

RELINING FOR PROSTHESES AND PROCESS THE MANUFACTURING THEREOF

FIELD OF APPLICATION

The invention pertains to a relining for prostheses on the basis of silicone and an adhesive for a durable bond between the plastic of the prosthesis and the silicone.

When bonding silicones with plastics, in particular in dentistry the problem is to obtain a stable, durable, and stable bond. Thus, the dental prosthesis is provided with a relining material of the relining in order to maintain the functional efficiency of dental prostheses due to changes of the prosthesis support.

With regard to materials science, hard and soft-remaining materials used for relining a dental prosthesis should have a good adhesion to the plastic of the prosthesis, a sufficient dimensional stability, a low water absorption, a high abrasion resistance under oral conditions and a smooth surface. With regard to clinical practice, demands for biocompatibility, freedom from odour and taste, resistance to fungi and bacteria, colour fastness, an aesthetic appearance and a high ease of cleaning are added. An additional demand is the fast execution of relining including the functional shaping in the so-called direct relining method in one operating step at the dentist without any detour via a dentistry laboratory.

Further, a good processability with dental instruments such as, e.g., milling cutters, scalpels, polishing disks is highly important.

By a good processability there is understood that the cured relining material can be routed with rotating instruments, i.e., slipping off with the milling cutter, an erasing effect or a breakaway of larger silicone parts will not occur.

As relining materials natural rubber, polyvinyl compounds, fluorocarbon elastomers, hard and soft-remaining acrylic acid derivatives and silicones have been known in the prior art.

The known soft-remaining materials inhere drawbacks such as a short shelf live, an insufficient adhesion to the base of the prosthesis, embrittlement, discolouration and others. Of the proposed materials, acrylic acid with plasticizers and silicones are used most frequently for the soft-remaining relining. However, the common characteristics of acrylic acid derivatives are unsatisfactory. Although said derivatives provide a very good binding and consequently adhesion to the prosthesis plastics due to the similar composition thereof, the plasticizer contained therein, however, will diffuse out over time which will result in embrittlement, dimensional changes and porosity of the relining material. In addition, due to the toxic effect of the monomer components on the mucous membrane acrylic acid derivatives can be used only restrictedly for the direct relining method within the mouth of the patient. The indirect relining brings about a laboratory operating step with possible sources of error, a second treatment attendance, and the patient has to manage without his prosthesis for a longer time.

Recently, hardening (meth)acrylic acid derivatives have normally been used for the hard relining. Although they bond well to the prosthesis plastics, they are used nearly exclusively for the indirect relining method due to the drawbacks described above. In addition, when using said materials in the direct relining method a removal from the mouth without any difficulty, e.g., with partial prosthesis, would be endangered due to the inflow of material into cavities.

Regarding the requirements on a relining material in the direct process, silicones are most suited. However, the adhesion thereof to the prosthesis plastic of poly methyl methacrylate turned out to be extremely unsatisfactory. According to the prior art, a reduction of this unwanted effect is achieved by mechanical retentions and the use of adhesion promoters consisting of a mixture of acrylooxyalkylsilanes, e.g., methacryloxypropyltrimethoxy-silane. However, the bond strengths obtainable thereby are still below 100 $Ncm^{-2}$.

From DE-A-39 02 817 it is known that the adhesion of addition crosslinking silicones to the prosthesis plastic by adding from 10 to 50% by weight of a powdery methacrylate (co)polymer as a filler to a heat-curing vinylsilicone mass of the addition polymerization type can result in bond strengths of up to 200 $Ncm^{-2}$. However, due to the high amount of methacrylate plastic the typical properties of the silicone important for relining materials such as the permanent flexibility and the water-repellent effect are partially lost so that a durability of only six months can be specified for such a relining material.

DE-A-39 11 520 describes a permanently durable and soft-remaining relining on the basis of silicone rubber. Here, the adhesion between the prosthesis plastic and the silicone is achieved by vulcanizing the silicone on a steel reinforcement at 200° C. and subsequently applying the prosthesis plastic and the teeth on the steel basis. A drawback in this process are the high required temperatures and the required expenditures in equipment.

In PCT/EP 950 13 13 and DE-A-195 39 653 two-component polyurethane adhesives with an addition of organohydrogenpolysiloxanes for the durable bonding of prosthesis plastics with addition-crosslinking silicones are described.

Said system provides good adhesive bonds which inhere, however, all known drawbacks of a two-component system as compared with a one-component system: higher expenditures in time for mixing both components homogeneously and higher expenditures in time due to the necessary reaction times of both components reacting with each other, the risk of mixing inhomogeneities, wrong metering and the incorporation of air.

Moreover, with two-component polyurethane systems there is the risk of foaming and gassing depending on the air humidity of the environment.

EP-A-0 632 060 describes the use of silicone-modified acrylic copolymers having mean molecular weights from 5,000 to 1,000,000 g/mol as one-component adhesive (constituent part of commercial product 1, see table 1–4) which is manufactured by the copolymerisation of methyl meth-acrylate with allyl methacrylate and the subsequent platinum-catalysed hydrosilylation of the prepared copolymer containing allyl groups with a hydrogen polydimethyl-siloxane.

However, the amount of syntheses for this adhesive is high.

On the one hand the copolymerisation catalysts interfere with the platinum-catalysed hydrosilylation, and on the other hand the consumed platinum catalyst has to be removed from the product after the hydrosilylation in order to avoid stability problems due to the development of hydrogen.

According to EP-A-0 614 655, the adhesive force obtainable with this adhesive results in a bond between the PMMA plastic and the appropriate relining silicone (constituent part of commercial product 1).

The fracture stress values of this adhesive bond as determined in the tensile test are between 67 and 75 N/cm$^2$ (see table 2a). The fracture pattern demonstrates a pure cohesive failure in the silicon, however, from the above-mentioned fracture stress it can be concluded that the tear strength of the relining silicone according to EP-A-0 614 655 (constituent part of commercial product 1) has comparatively low values such that a high tear strength and the tear propagation resistance for the employed relining silicone is ensured only insufficiently to resist the permanent load of the chewing motion in a long-term relining.

Further, the relining silicone of commercial product 1 on the basis of EP-A-0 614 655 demonstrates a very high (not user-friendly) resistance to a manually implied force during the discharge from a cartridge. (See table 1, comparative tests.)

Favourably the relining silicone is metered and mixed by means of a hand-operated discharge gun from a cartridge having a static mixer. Here, it is important that the required resistance to a manually implied force necessary to discharge the relining silicone be as low as possible in order to ensure a user-friendly operation.

Under the mentioned conditions the relining silicone according to EP-A-0 614 655 (see commercial product 1) does not present a sufficiently long pot life such that the mimic motions of the patient can be reproduced only insufficiently here. However, for a direct relining of the prosthesis in the dentist's practice (chairside) a sufficiently long pot life of the relining material under oral conditions (35° C.) is necessary.

In addition, during the functional impression said relining silicone (see commercial product 1) can flow into the pharyngeal cavity of the patient due to the low static stability thereof.

However, for the functional impression a high static stability of the relining silicone during the pot life is necessary in order to avoid an unwanted outflow of the material from the area to be relined. In addition, there is the risk that the layer thickness of the relining turns out to be too low to ensure the fitting accuracy and the wear comfort of the relined prosthesis.

The tear strength and the tear propagation resistance of the two-component relining silicone to be employed according to JP 07291820 A, also designated as "coat", "polish", "glazing", are not sufficient as well. After vulcanizing said relining silicone has an insufficient elasticity and is very brittle. (See table 4, comparative tests.)

At present, other relining systems meeting the requirements on the total system only with restrictions exist on the market.

Thus, the viscosity of the relining material of the commercial product 2 (see table 1 to 4) is too low to perform a correct functional impression. For the reasons stated above, a comfortable, well-fitting relining can be manufactured from this material only with difficulties.

After processing according to the manufacturer's package circular, the required adhesive bond of the pertinent relining adhesive between the prosthesis plastic and the relining plastic is not established completely after the end of the specified setting time. Shear tests (tables 2a/2b, comparative tests) show on the basis of the fracture pattern that there is no exclusive cohesive failure within the relining silicone but a portion of the adhesive bond between the relining silicone and the prosthesis plastic fails.

Hence, when processing the relining with a scalpel or a milling cutter after the specified setting time, there is the risk that the adhesive bond between the relining silicone and the prosthesis plastic is irreversibly damaged and the effected areas become starting points for the attack of water, bacteria, and fungi under oral conditions so that such a relining will resist the permanent load of a long-term use only insufficiently. After vulcanization, the two-component sealing lacquer of the commercial product 2 exhibits a high inherent tackiness and a comparatively low tear strength and tear propagation resistance (see table 4).

Tests of commercial product 3 (see tables 1 to 4) according to the requirements of the package circular reveal an insufficient matching between the setting behaviour of the relining silicone and the formation of the adhesive bond between the relining silicone and the prosthesis plastic.

After the specified 5 min residence time in the mouth the adhesive bond between the relining silicone and the prosthesis plastic is not completely provided. The fracture pattern obtained from tensile tests reveals that the bond between the prosthesis plastic and the relining silicone fails partially. A prosthesis relined in this manner meets the requirements of a long-term permanent load only insufficiently since after a short time under oral conditions the penetration of water, contaminations, bacteria, and fungi between the prosthesis plastic and the relining silicone and subsequently a separation of the relining from the basis of the prosthesis will have to be expected.

The preparation of a relining at the dentist or the dental technician should be feasible in a reasonable time. With the relining sealing lacquer of commercial product 3 the curing takes about 30 min at room temperature whereby the patient's waiting time and the dentist's or dental technician's work will be extended unnecessarily.

Moreover, after the vulcanization the two-component relining sealing lacquer reveals an insufficient elasticity and is very brittle (see table 4).

DE-A-19 614 983 describes a soft relining material for prostheses which does not separate from the prosthesis. This document, however, does not disclose how the adhesive bond between the prosthesis plastic and the relining silicone is provided.

However, comparative experiments show that relining silicones of the described type do not adhere to prosthesis plastic without a relining adhesive. Tensile tests reveal a moderate adhesive bond with a fracture pattern having a non-cohesive fracture between the relining silicone and the prosthesis plastic. A prosthesis relined according to DE-A-19 614 983 can withstand a long-term permanent load only to a limited extent.

Hence, it is the object of the invention to provide a relining for prostheses and a process for the manufacturing thereof which is improved over the state of the art with regard to the performance of the items long-term stability, a high tear strength and tear propagation resistance and with that a good processability by dental instruments such as milling cutters, scalpels, polishing disks and an easily available, strong adhesive bond to the prosthesis plastic and a strong adhesive bond to other dental substances such as metals, metal alloys, ceramics, and glasses and with regard to the application-technical properties of the individual components such as flow behaviour, i.e. viscosity, static stability, dischargeability, and setting characteristics, i.e. processing time, completion of setting.

This object is achieved by the features of claims 1 and 10.

According to the invention a relining consisting of a one-component relining adhesive, a two-component addition-crosslinking relining silicone and an two-component addition-crosslinking sealing lacquer is provided.

The one-component relining adhesive consists of a mixture of the invention made from (meth)acrylic esters and a functionalised silane comprising methacrylate and other unsaturated groups, which quickly provides a strong and stable adhesive bond between the prosthesis plastic and the relining silicone or the relining sealing lacquer already at room temperature.

The two-component addition-crosslinking relining silicone contains organohydrogenpolysiloxanes having a high SiH content resulting in a very strong adhesive bond with the "relining adhesive" functional unit of the invention (see table 2a, 2b, 3) and organohydrogenpolysiloxanes having a comparatively low SiH content providing a high elasticity and tear strength of the relining silicone and only because of this a good mechanical processability, e.g., by rotating dental instruments (see table 1).

Due to the use of the organohydrogenpolysiloxanes having a high SiH content and organohydrogenpolysiloxanes having a comparatively low SiH content which results in a comparatively high elasticity and tear strength, the solvent-free, two-component, addition-curing relining sealing lacquer is distinguished by a very high adhesive force to the relining adhesive and the relining silicone at a very low viscosity (brush application) (see table 4).

In spite of the very low viscosity of the mixture that can be applied using a brush, which is achieved without the use of solvents, the sealing lacquer can be discharged and homogenized from double chamber cartridges by static mixers such that an inclusion of air bubbles is excluded.

The relining of the invention achieves the object taking into account other mechanical and easy to process characteristics relating to appropriately processible viscosities/consistencies with the standard dosing and mixing systems (see table 1), practice-orientated setting behaviour, processability, static stability, and flow behaviour during the pot life and the functional impression and a smooth surface finish of the cured relining silicone/relining sealing lacquer in order to achieve an improved relining.

Further the constituent formulations have a sufficient shelf life within the appropriate primary package such as, e.g., a cartridge, tube, or bottle.

The one-component relining adhesive of the invention is applicable in all fields where silicones are to be adhered to plastics, metals, metal alloys, ceramics, and glasses.

The one-component relining adhesive is preferably used in dentistry and epithetics.

The one-component relining adhesive improves the adhesive bond between silicone and the prosthesis plastic under room temperature conditions to a high degree by providing a strong adhesive bond to the relining silicone or the relining silicone sealing lacquer of the invention after the application to a prosthesis plastic. Thus, the advantageous properties of silicones as relining materials are utilized.

Another advantage of the one-component relining adhesive of the invention is the suitability for adhering prostheses which contain metallic (alloy) or ceramic components in addition to the prosthesis plastic. In this case the prosthesis provided with an adhesive is annealed at temperatures >30° C. for some minutes.

This provides a good adhesive bond between the metallic and/or ceramic components and the silicone.

Hence, providing a one-component relining adhesive which is suited for adhering plastics, in particular PMMA, with silicon and provides a good adhesive bond both to the (prosthesis) plastic and to silicone is planned.

Applying the relining adhesive of the invention in a dissolved form to the (prosthesis) plastic to be bonded is especially advantageous since the solvent evaporates off rapidly depending on the volatility thereof (e.g., dichloromethane within 90 seconds) and therefore in a very short period of time a conditioned (prosthesis) plastic surface is provided which can be coated with the relining silicone of the invention without further delay.

Another advantage is that immediately after the curing of the relining silicone of the invention on the surface of the (prosthesis) plastic conditioned with the relining adhesive of the invention a very strong adhesive bond is achieved which enables a rapid, practice-orientated processing, e.g., with a milling cutter.

Thus, a rapid and efficient relining of the dental prosthesis both directly at the dentist and indirectly at the dental laboratory is possible.

Investigations show that the relining adhesive of the invention ensures durable, strong adhesive bonds with all standard prosthesis plastics, e.g., cold-cured resins, hot-cured resins, and injection-mould plastics; see table 2b.

The structural features of the adhesive component Z of the invention are as follows:

a) an ethylenically unsaturated compound such as, e.g., of the type

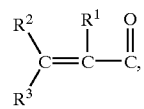

wherein:
$R^1$: H, halogen, alkyl, substituted alkyl, CN
$R^2$, $R^3$: H, halogen, alkyl, substituted alkyl;
e.g.: α-methylvinylcarbonyl
β-methylvinylcarbonyl
vinylcarbonyl
vinyl;

b) B=O, S, NH, NR, PH, PR c) A=spacer of a straight-chained or branched hydrocarbon moiety having from 0 to 30 C atoms which can also contain an aromatically unsaturated or cycloaliphatic ring;

d) polydialkylsiloxy: e.g.: polydimethylsiloxy of the type

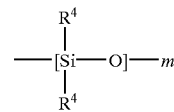

e) a siloxane containing a trifunctional T and/or a tetrafunctional Q unit, wherein $R^4$ in items d) and e) is an unsaturated group, e.g., alkenyl, alkinyl, alkenyloxy, alkinyloxy, e.g., vinyloxy and allyloxy, wherein the above-mentioned groups can be cyclic, linear as well as branched, and/or one of the following groups:
alkyl (e.g., methyl, ethyl, isopropyl), aryl (e.g., phenyl, naphthyl, tolyl, xylyl), aralkyl (benzyl, phenylethyl) and halosubstituted alkyl and aryl groups (e.g., 3,3, 3-trifluoropropyl, chlorophenyl, difluorophenyl), cyanoalkyl, cycloalkyl), wherein $R^5$ may be equal to $R^4$ or $R^6$;
wherein $R^6$ is composed of the moieties described under 2.1a) to d).

The structural features of items a) to e) combine to yield the following general formula:

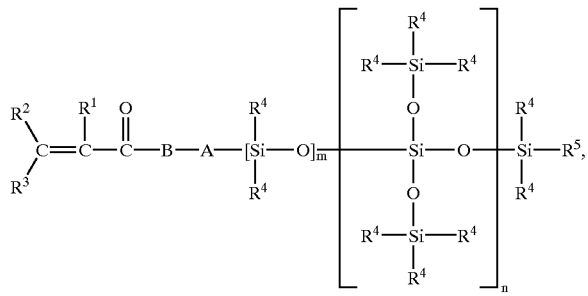

wherein n and m are integers within the range from 0 to 1000.

The one-component relining adhesive of the invention can be employed in the form of the pure adhesive component Z or as a copolymer containing the adhesive component Z or as a mixture of the copolymer with the starting material (adhesive component Z, monomers).

For example, the copolymer is synthesized as follows:
the adhesive component Z is polymerized with suitable monomers such as acrylate or methacrylate.

Methacrylates and acrylates, preferably mono or polyfunctional methacrylates, especially alkyl methacrylate, cycloalkyl methacrylate, isoalkyl methacrylate, tetraethylene glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate, dodecanediol dimethacrylate, bisphenol A dimethacrylate, trimethylolpropane trimethacrylate, 2,2-bis-4(3-methacryloxy-2-hydroxy)phenylpropane(bis-GMA) and reaction products from di and/or triisocyanates and OH group-containing methacrylates.

The reaction can be performed as a cold, a hot polymerization or a photopolymerization.

As the catalyst for the hot polymerization of the ethylenically unsaturated monomers the conventional catalysts, e.g., peroxides such as dibenzoyl peroxide, dilauryl peroxide, tert-butyl peroctoat, tert-butyl perbenzoate, but also $\alpha,\alpha'$-azobis(isobutyro ethyl ester), AIBN, benzpinakol, and 2,2'-dimethylbenzpinacol are suitable.

As the catalyst for the cold polymerization of the ethylenically unsaturated monomers the conventional catalysts, in particular amine/peroxide systems (e.g., dibenzoyl peroxide/N,N-dimethyl-p-toluidine) are suitable.

As the catalyst for the photopolymerization of the ethylenically unsaturated polymers benzophenone and the derivatives thereof, benzoin and the derivatives thereof, acylphosphine oxides, especially $\alpha$-diketones such as camphorquinone, optionally combined with an amine as reducing agent, are suitable.

The following processes are used as polymerization processes:

Bulk polymerization, solution polymerization (e.g., toluene, chloroform, methylene chloride), precipitation polymerization (in pure solvents or solvent mixtures such as, e.g., methylene chloride/hexane), and suspension polymerization (e.g., water with surfactants, emulsifiers).

The one-component relining adhesive of the invention can be used in the form of the pure adhesive component Z or as a copolymer containing said adhesive component Z or as a mixture of said copolymer with the starting materials (adhesive component Z, monomers).

Preferably, the following composition is used:
In a dissolved form

| a) | adhesive component Z as a pure substance | 0–99% by weight |
| b) | copolymer with the adhesive component Z as a component | 0–99% by weight |
| c) | copolymer in admixture with the starting materials (adhesive component Z, monomer), | 0–99% by weight | wherein the sum of the parts by weight of components a), b), and c) is at least 0.01% by weight.

| d) | catalysts for accelerating the formation of the adhesive bond to the silicone to be bonded | 0–10% by weight |
| e) | solvent | 1–99.99% by weight |
| f) | colouring agents | 0–20% by weight |
| g) | surfactants, emulsifiers, and stabilizers | 0–20% by weight |
| h) | organohydrogensiloxane | 0–40% by weight |
| i) | $\alpha,\omega$-divinylpolydialkylsiloxane | 0–40% by weight |

The adhesive component Z as a pure substance a) is composed according to the general formula described above.

The copolymer b) containing the adhesive component Z is prepared by polymerizing as described above.

The mixture c) of the copolymer with the starting materials (adhesive component Z and monomer) consists of the following components:

| the copolymer | 0.1–99.9% by weight |
| the adhesive component Z | 0.1–99.9% by weight |
| the monomer | 0.1–99.9% by weight, | the sum of the three components being 100%.

As catalysts for accelerating the formation of the adhesive bond to the silicone 1d) to be bonded salts, complexes and colloid forms of the transition metals of the 8th subgroup, preferably those of the platinum, palladium and rhodium metals, are used; in particular platinum complexes prepared from hexachloroplatinic acid and radical-forming substances such as peroxides, preferably diaroyl, dialkyl, diaralkyl, alkylaralkyl, alkylaroyl peroxides and sulfur have proven to be suitable.

As the solvent e) all organic solvents such as aromatics, petroleum spirits, ethers, esters, alcohols, ketones, aldehydes, amines, carboxylic acids, halogenated solvents, e.g., chloroform and water and the possible combinations of the above-mentioned solvents can be used.

The colourants mentioned under f) are soluble colourants or pigment colourants. In the field of dental and medical applications of the adhesive exclusively food colourants approved by the BGA (Federal German Public Health Office) as such are used. Colour pastes made of polysiloxane, mineral oil, food colourant formulations are used as well.

The components g) used as emulsifiers and stabilizers are anionic surfactants, especially alkyl sulfates, alkyl benzene sulfonates and phosphates, cationic surfactants, especially tetraalkyl ammonium halides, tetraalkyl ammonium sulfates, or tetraalkyl ammonium acetates or alkylpyridinium halides, nonionic surfactants, especially alkyl and alkyl phenyl polyethylene glycols and alkyl phenyl polyethylene glycol ethers, fatty acid alkylolamide, sucrose fatty acid ester, trialkylamine oxide, silicone surfactants or fluoro surfactants and amphoteric surfactants, especially sulfated or oxyethylated condensation products from alkyl phenoles and formaldehyde, ethylene oxide-propylene oxide block polymers, modified polysiloxanes, polyvinyl-N-alkylpydidinium salts or copolymers from vinylpyridine and methacrylic acid. The surfactants may also contain functional groups such as, e.g., —OH, —CH=CH$_2$, —OCO—(CH$_3$)C=CH$_2$, SiH, and —Si—CH=CH$_2$.

The organohydrogensiloxane components h) serve as crosslinking agents, and they are polyalkyl and polyarylsiloxanes and polyhalogenalkyl and polyhalogenarylsiloxanes having at least two hydrogen atoms bonded to silicon atoms. Crosslinking agents having a SiH content from 1 to 15 mmol/g, preferably from 2 to 11 mmol/g are used.

The organopolysiloxanes i) having two vinyl groups within the molecule have a viscosity between 21 and 200,000 mPa·s.

The epithetic/relining silicone is an addition-crosslinking silicone consisting of two components which chemically crosslink via a noble metal-catalysed hydrosilylation reaction.

The components A and B are adjustable in various viscosities (low-, medium-viscous, viscous and kneadable) and mixing ratios (normally 1:1). The mixing of components A and B, by weight or by volume, is performed in suitable metering and mixing devices such as, e.g., strand length metering and manual mixing, a cartridge system using a static mixer and electrically/mechanically operated mixers. After metering and mixing the components A and B the resulting, homogeneously mixed paste is applied to the mouth of the patient with suitable auxiliary devices within the total processing time. Subsequently the patient does functional motions which influence the shape of the relining silicone material, which can function as the functional impression at the same time, during the processing time.

After the curing of the material (residence time within the mouth) said material is removed from the mouth of the patient and processed according to the requirements.

The silicone material of the invention is distinguished as compared with the state of the art in particular by a high tear strength and an outstanding adhesive bond to the relining adhesive in the vulcanized state.

Surprisingly, it has turned out that the chain length, the SiH content and the concentration of the organohydrogenpolysiloxane exert a great influence on the adhesive force to the one-component relining adhesive of the invention and on the tear strength as well.

Further, in addition to a practice-orientated processability and a good flow behaviour during the processing time the relining silicone of the invention is distinguished by a patient-friendly setting within the mouth and a sufficiently long processing time within the mouth so that the patient can perform his functional motions.

In addition, the inventive composition of the silicone material on the basis of organopolysiloxanes having two vinyl groups within the molecule and a viscosity from 21 to 200,000 mPa·s realises both a soft-remaining (low Shore hardness) and a very hard (high Shore hardness) relining silicone. Despite the high vinyl content the hard relining silicone does not exert an inhibiting action on the vulcanizing rate. In combination with the SiH crosslinking agent and the platinum catalyst vulcanisations having a user-friendly setting characteristics are realized.

Due to the strong adhesive bond a selective processability (e.g., by a scalpel, a milling cutter) of the excessive silicone material cured within the mouth is feasible so that the relining silicone can exactly be adapted to the individual contours of the mouth and the jaw without the relining silicone separating from the adhesive bond to the dental prosthesis during the processing (see examples 3, 4, 5, and 8).

Further, the silicone material of the invention does not exhibit any decrease of the adhesive bond to the one-component relining adhesive of the invention after a storage in water (see table 3).

The tear strengths and requirements on the adhesive bond under wet oral conditions are achieved while maintaining the other mechanical and easy to process properties with respect to appropriately processible viscosities/consistencies by the above-mentioned metering and mixing systems, a practice-orientated setting behaviour, flexibility, processability, release properties, flow behaviour during the processing time and optionally a smooth surface finish. Nonetheless, the formulation of the ingredients has a sufficient shelf life within the appropriate primary package such as, e.g., a cartridge or tube, where in this connection by the shelf life there is understood for example the maintaining of the performance characteristics with regard to the viscosity/consistency of the individual components and the mixture and the setting characteristics for a minimum of 12 months before and during the vulcanization and with regard to the tear strength and the adhesive force for a minimum of 12 months after the vulcanization.

The relining silicone of the invention has the following composition of ingredients and the following amounts of individual components a) to o) in % by weight, based on the entire silicone material:

a1) from 0.1 to 80% by weight, preferably from 1 to 40% by weight of organohydrogenpolysiloxanes and mixtures thereof having a SiH content from 2.00–15 mmol/g, preferably from 3.0–11.0 mmol/g and a viscosity from 10 to 10,000 mPa·s, preferably from 30 to 500 mPa·s;

a2) from 0.1 to 80% by weight, preferably from 1 to 40% by weight of organohydrogenpolysiloxanes and mixtures thereof having a SiH content from 0.03–2.0 mmol/g and a viscosity from 10 to 70,000 mPa·s, preferably from 30 to 2000 mPa·s;

b) from 1 to 90% by weight, preferably from 10 to 60% by weight of organopolysiloxanes having two vinyl groups within the molecule and a viscosity from 21 to 200,000 mPa·s;

c) from 0.0001 to 1.0% by weight, preferably from 0.0005 to 0.2% by weight of catalysts for accelerating the hydrosilylation reaction, based on the pure metal;

d) from 0 to 80% by weight, preferably from 0 to 50% by weight of the reinforcing fillers;

e) from 0 to 90% by weight, preferably from 20 to 80% by weight of the non-reinforcing fillers;

f) from 0 to 10% by weight, preferably from 0 to 2% by weight of the colourants;

g) from 0 to 50% by weight, preferably from 0 to 10% by weight of the moisture binders;

h) from 0 to 70% by weight, preferably from 0 to 20% by weight of organopolysiloxanes containing more than two vinyl groups per molecule;

i) from 0 to 1.0% by weight, preferably from 0 to 0.1% by weight of the inhibitors;

j) from 0 to 90% by weight, preferably from 0 to 50% by weight of the vinyl group-containing solid or liquid MQ silicone resin;

k) from 0 to 80% by weight, preferably from 0 to 50% by weight of a compound of vinyl group-containing organopolysiloxanes and reinforcing fillers;

l) from 0 to 10% by weight, preferably from 0 to 5% by weight of the surfactants, emulsifiers and stabilisers;

m) from 0 to 90% by weight, preferably from 0 to 80% by weight of the radiopaque substances;

n) from 0 to 20% by weight, preferably from 0 to 10% by weight of the $H_2$ absorbing/adsorbing substances or the substances reducing or eliminating the development of $H_2$;

o) from 0 to 50% by weight, preferably from 0 to 35% by weight of the plasticizers, neutral oils and distributing oils.

The relining silicone of the invention contains organohydrogen-polysiloxanes a1) having a high SiH content (from 2.0 to 15.0 mmol/g SiH, based on the polymer, especially preferred from 2.0 to 9.5 mmol/g) and a viscosity from 10 to 10,000 mPa·s, preferably from 30 to 500 mPa·s resulting in a very strong adhesive bond to the one-component relining adhesive of the invention.

In addition, a high elasticity and tear strength is achieved by adding organohydrogenpolysiloxanes a2) having a comparatively low SiH content (from 0.03 to 2.0 mmol/g SiH, based on the polymer) and a viscosity from 10 to 70,000 mPa·s, preferably from 30 to 2000 Pa·s.

The above-mentioned organohydrogenpolysiloxanes a1) and a2) can have the following structure:

A. Structural formula of the linear organohydrogensiloxanes

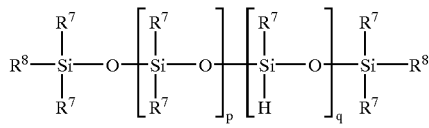

with p=0–1500 with q=0–1500 with $R^7$=alkyl (e.g., methyl, ethyl, isopropyl), aryl (e.g., phenyl, naphthyl, tolyl, xylyl), aralkyl (benzyl, phenylethyl) and halo substituted alkyl and aryl groups (e.g., 3,3,3-trifluoropropyl, chlorophenyl, difluorophenyl), cyanoalkyl, cycloalkyl, and cycloalkenyl. Preferably is R=methyl.

with $R^8=R^7$, H.

B. Si—H containing MQ resins consisting of:

$(R^7)_3SiO_{1/2}$, $(R^7)_2(H)SiO_{1/2}$ and $SiO_{4/2}$ units.

Moreover, the trifunctional $R^8SiO_{3/2}$ can be present as T units and the bifunctional $R^7R^8SiOS_{2/2}$ can be present as D units, wherein $R^7$ and $R^8$ have the meaning defined in A.

The risk of an evolution of gas, i.e. the cleavage of $H_2$ from the organohydrogensiloxanes, which may be caused by impurities and residual amounts of, e.g., acids, bases, and metals incorporated during the manufacturing process is minimized or excluded by the high purity, the selected concentrations, based on the overall formulation, and the optimal SiH content.

Moreover, all other precautions known in the art can be taken to avoid an evolution of gas.

The vinyl containing organopolysiloxanes b) having two vinyl groups in the molecule have the following general formula:

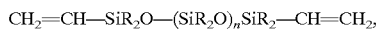

wherein

R=alkyl (e.g., methyl, ethyl, isopropyl), aryl (e.g., phenyl, naphthyl, tolyl, xylyl), aralkyl (benzyl, phenylethyl) and halo substituted alkyl and aryl groups (e.g., 3,3,3-trifluoropropyl, chlorophenyl, difluorophenyl), cyanoalkyl, cycloalkyl, and cycloalkenyl. Preferably is R=methyl, n=an integer having a value from 21 to 1500, wherein 'n' represents theoretically calculated values calculated from the experimentally determined vinyl content on the assumption that each molecule contains two vinyl groups and R=methyl.

As hydrosilylation catalysts c) salts, complexes, and the colloidal forms of the transition metals of the 8th subgroup of the periodic table, preferably the platinum, palladium, and rhodium metals are suited; in particular platinum complexes prepared, e.g., from hexachloroplatinic acid or from platinum salts are suited. Said catalysts can also be applied on support materials such as, e.g., zeolites or carbon.

The component d) is a highly dispersed, active filler having a BET surface of at least 25 $m^2/g$, such as titanium dioxide, aluminium oxide, zinc oxide, and preferably wet-precipitated or pyrogenically obtained silicic acid.

The mentioned substances can be hydrophilic or hydrophilized.

Further, fibrous or lamellar fillers can be used as reinforcing fillers, with mineral, fibrous fillers such as, e.g., wollastonite, and synthetic, fibrous fillers such as, e.g., glass fibres, ceramic fibres, or plastic fibres being used.

Reinforcing fillers are incorporated in the formulation to improve the sedimentation behaviour of optionally included non-reinforcing fillers and to adjust the rheological properties such as the viscosity and the thixotrophy.

Fillers e) are incorporated in the formulations to obtain more cost efficient formulations and to control the mechanical properties within narrow limits.

Metal oxides, metal hydroxides, mixed oxides, and mixed hydroxides, preferably silicon dioxide, especially in the form of quartz and cristabolite, and aluminium oxide, calcium oxide, aluminium hydroxide are used.

Also fillers such as calcium carbonate, kieselguhr, diatomaceous earth, talcum, glass and fillers on the basis of plastics, e.g., polymethyl methacrylate bead polymer, polycarbonate, polyvinyl chloride, silicone resin powder, powders on the basis of fluoroorganic compounds and inorganic and organic spherical fillers and fibres (are used).

The fillers mentioned under d) and e) can also be surface treated (coated). The surface treatment can be effected, e.g., by silanes and fatty acids having functional groups which in turn can react with the reactive components a), b), and c), for example

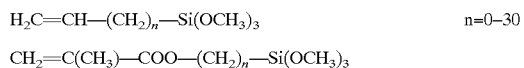

$CH_2=C(CH_3)—COO—(CH_2)_n—Si(OCH_3)_3$

The colourants mentioned under f) are the same compounds described with the relining adhesive under f).

Zeolites, anhydrous aluminium sulfate, molecular sieve, kieselguhr, and blue gel may be used as moisture binder g). The effect of the moisture binders is based on the selective adsorption of water molecules.

The organopolysiloxanes containing more than two vinyl groups in the molecule mentioned under h) are vinyl-terminated or vinyl side-chain organopolysiloxanes having a viscosity from 20 to 350,000 mPa·s.

As inhibitors i) for adjusting the reactivity of the hydrosilylation reaction short-chain organopolysiloxanes of the general formula

are used, wherein

R are equal or different, optionally substituted hydrocarbon moieties such as, e.g., alkyl, alkenyl, alkinyl and n=0 or an integer from 1 to 6.

Further, R can be an alkenyl-terminated or alkinyl-terminated siloxane moiety.

Further, vinyl-containing, cyclic siloxanes such as, e.g., tetravinyltetramethylcyclotetrasiloxane or organic hydroxyl compounds containing terminal double or triple bonds can be used to control the crosslinking rate.

The solid or liquid MQ resins containing vinyl and ethoxy groups mentioned under j) are characterized in that they contain the tetrafunctional $SiO_{4/2}$ as the Q unit and the monofunctional $R_3SiO_{1/2}$ as M units, wherein R can be vinyl, methyl, ethyl, phenyl.

Moreover, the threefunctional $RSiO_{3/2}$ can be present as T units and the bifunctional $R_2SiO_{2/2}$ can be present as D units with R having the same meaning as defined above.

These MQ resins can be dissolved in organopolysilixanes having two or more vinyl groups within the molecule and a viscosity from 21 to 350,000 mPa·s.

The vinyl group content of the above-mentioned MQ resins is within the range from 0.1 to 8 mmol/g, and the ethoxy group content is below 4 mmol/g. The SiOH content of the MQ resins is so low that there is no gas evolution due to the formation of hydrogen gas.

Further, the amount of volatile components of the MQ resins is so small that the dimensional stability is not impaired.

The compounds k) are composed of organopolysiloxanes having two or more vinyl groups within the molecule and a viscosity from 21 to 350,000 mPa·s and the reinforcing fillers mentioned under d). Said compounds can be hydrophilized in situ using modifying auxiliaries, e.g., hexamethyldisalazane.

The components l) used as surfactants, emulsifiers, and stabilizers are the same compounds described with the relining adhesive under j).

The radiopaque substances specified under m) are barium, strontium, lanthanum or zinc containing glasses, barium sulfate, zirconium dioxide, lanthanum oxide or ceramic filler compositions containing oxides of lanthanum, hafnium, and rare earth metals.

Further, complex heavy metal fluorides of the general formula $M^{II}M^{IV}F_6$ or $YF_3$, wherein $M^{II}$ represents a calcium, strontium, or barium ion and $M^{IV}$ represents a titanium, zirconium, or hafnium ion may be used.

Further, atoms or atom groups bonded to the silicone polymer having radiopaque properties, such as, e.g., iodine bonded to silicon may be used.

The $H_2$ absorbers/adsorbers mentioned under n) are finely divided palladium of platinum or alloys thereof, said substances optionally being incorporated in alumosilicates.

Further, substances eliminating or reducing the evolution of $H_2$ such as, e.g., 3-methyl-1-butine-3-ol and $CH_3Si[O—C(CH_3)_2—C\equiv CH]_3$ are usable as well.

The plasticizers, neutral and distributing oils mentioned under o) are trimethylsiloxy-terminated polydimethylsiloxanes, hydrocarbons (mineral oils, waxes), paraffin jelly, esters such as adipates, benzoates, butyrates, acetates, esters of higher fatty acids, peroxidised fatty acid esters, glycolates, higher-molecular esters (polymer plasticizers), phosphoric esters, propionic esters, sebacic esters, sulfonic esters, trimellitic esters, citric esters, abietinic esters, azelaic esters, ketones such as, e.g., camphor, chlorinated hydrocarbons, polyols, and polyol ethers.

The relining sealing lacquer of the invention consists of two components which chemically crosslink through a noble metal-catalysed hydrosilylation reaction.

Components A and B of the relining sealing lacquer can be adjusted in various mixing ratios. Usually, both components are mixed in a 1:1 mixing ratio, by weight or by volume, in suitable metering and mixing devices such as strand length metering and manual mixing systems, cartridge systems comprising static mixers or electrically/mechanically operated mixers.

The viscosities of components A and B and the viscosity of the homogeneous mixture of A and B at the time after completion of the mixing are preferably adjusted to 25–10,000 mPa·s. Thus, it is ensured that the relining sealing lacquer can be applied by appropriate auxiliary devices such as a brush, a sponge, or a spatula to the areas of the relined prosthesis to be sealed in a very thin layer during its pot life.

In order to exactly adjust the relining silicone material cured in the mouth to the individual contours of the mouth and the jaw during the preparation of a relining, the material has to be processed by a milling cutter or a scalpel.

The roughened surfaces of the relining "damaged" by this mechanical processing and the transition zone between the relining adhesive and the relining silicone can be sealed by the relining sealing lacquer of the invention by applying a thin layer of the homogeneously mixed paste during the total pot life.

Thus, porosities and roughnesses which might promote an accumulation of plaque, food particles, bacteria, and fungi are avoided. At the same time, by avoiding roughnesses the wear comfort of the relined prosthesis is increased since the sealed areas reduce the friction between the relined prosthesis and the mucous membrane. Hence, the mucous membrane of the mouth which is often damaged with patients needing a relining due to inflammations of the mucosa, sharp bone edges, fresh extractions or operating areas is additionally relieved, and so-called "erasing" effects are avoided.

The relining sealing lacquer of the invention is distinguished over the art by a particularly high tear strength and its smooth surface finish.

Surprisingly, it has been found that it is possible to obtain high tear strengths despite lowest viscosities of the relining sealing lacquer. The tear strengths of relining sealing lacquers in accordance with the prior art did not prove capable of surviving possible expanding, compressive, or bending motions without any damage. Due to the high brittleness thereof, crack formation can occur in the layer of the relining sealing lacquer after a mechanical load, which will render the relining susceptible to the accumulation of impurities.

The relining sealing lacquer of the invention meets the required tear strengths and the requirements on the adhesive bond to the functional units of the relining silicone and the relining adhesive while maintaining the other mechanical and easy to process properties with regard to viscosities which are usefully processible by the above-mentioned mixing and metering systems and application auxiliary devices such as brushes or sponges, a practice-orientated setting behaviour at room temperature, the flow behaviour during the total pot life and a smooth surface finish.

Further, the relining sealing lacquer is distinguished by a user-friendly setting on the surface to be sealed at room temperature in addition to a practice-orientated processability and a good flow behaviour during the pot life.

The described performance characteristics of the relining silicone lacquer further improve the wear comfort and the fitting accuracy of the relined prosthesis and result in a high acceptance by the patient.

Surprisingly, it has been found that a particularly high elasticity and tear strength as compared to the state of the art can be achieved by combining organohydrogenpolysiloxanes having a high SiH content (from 2.0 to 15 mmol/g), based on the polymer, and especially preferred between 3.0 and 11 mmol/g, with organohydrogenpolysiloxanes having a low SiH content (from 0,05 to 2 mmol/g).

The viscosities from 25 to 10,000 mPa·s required for a thin coatability of the relining silicone lacquer layer can be achieved by using appropriately short-chain organopolysiloxanes having two vinyl groups within the molecule.

The organohydrogenpolysiloxanes contained in the relining sealing lacquer ensure a high adhesive force both to the relining silicone and the relining adhesive.

In the appropriate primary packing (e.g., a tube or a cartridge) the formulations of the relining sealing lacquer have a sufficient shelf life. In this connection, by the shelf life there is understood for example the maintaining of the performance characteristics with regard to the viscosity of the individual components A and B and the mixture and the setting characteristics for a minimum of 12 months before and during the vulcanization and with regard to the tear strength and the adhesive force for a minimum of 12 months after the vulcanization.

Furthermore, the relining sealing lacquer does not reveal any decease of the tear strength after a storage in water and a boiling in water. The adhesive bond to the relining silicone and to the relining adhesive is maintained also after the above-mentioned treatment (see table 4).

According to the invention, the following composition of ingredients and the following amounts of the individual components from a) to n), by weight, based on the entire silicone material (components A and B), are used:

a1) from 0.1 to 80% by weight, preferably from 1 to 40% by weight of organohydrogenpolysiloxanes and mixtures thereof having a SiH content from 2.00–15 mmol/g, preferably from 3.0–11.0 mmol/g and a viscosity from 10 to 10,000 mPa·s, preferably from 30 to 500 mPa·s;

a2) from 0.1 to 80% by weight, preferably from 1 to 40% by weight of organohydrogenpolysiloxanes and mixtures thereof having a SiH content from 0.05–2.0 mmol/g and a viscosity from 10 to 10,000 mPa·s, preferably from 30 to 2000 mPa·s;

b) from 1 to 90% by weight, preferably from 10 to 60% by weight of organopolysiloxanes having two vinyl groups within the molecule and a viscosity from 21 to 200,000 mPa·s;

c) from 0.0001 to 1.0% by weight, preferably from 0.0005 to 0.2% by weight of catalysts for accelerating the hydrosilylation reaction, based on the pure metal;

d) from 0 to 80% by weight, preferably from 0 to 50% by weight of the reinforcing fillers;

e) from 0 to 90% by weight, preferably from 20 to 80% by weight of the non-reinforcing fillers;

f) from 0 to 10% by weight, preferably from 0 to 2% by weight of the colourants;

g) from 0 to 50% by weight, preferably from 0 to 10% by weight of the moisture binders;

h) from 0 to 70% by weight, preferably from 0 to 20% by weight of organopolysiloxanes containing more than two vinyl groups per molecule;

i) from 0 to 1.0% by weight, preferably from 0 to 0.1% by weight of the inhibitors;

j) from 0 to 90% by weight, preferably from 0 to 50% by weight of the vinyl group-containing solid or liquid MQ silicone resin;

k) from 0 to 80% by weight, preferably from 0 to 50% by weight of a compound of vinyl group-containing organopolysiloxanes and reinforcing fillers;

l) from 0 to 10% by weight, preferably from 0 to 5% by weight of the surfactants, emulsifiers, and stabilisers;

m) from 0 to 90% by weight, preferably from 0 to 80% by weight of the radiopaque substances;

n) from 0 to 20% by weight, preferably from 0 to 10% by weight of the $H_2$ absorbing/adsorbing substances or the substances reducing or eliminating the development of $H_2$;

The ingredients of the relining lacquer correspond to the ingredients of the relining silicone and the relining adhesive.

In order to manufacture the relining according to the invention, the areas of the PMMA prosthesis plastic to be bonded are initially cleaned and/or roughened, for example by abrasive corundum blasting using corundum with a particle size of about 100 $\mu$m and a pressure of 2 bars.

These areas are coated with the one-component adhesive of the invention in a layer thickness from 0.1 to 500 $\mu$m, preferably from 0.1 to 20 $\mu$m. Here, the adhesive of the invention can be applied in a liquid or dissolved form on the PMMA prosthesis plastic to be bonded. After the evaporation of the solvent the relining silicone of the invention can be applied immediately.

In order to accelerate the formation of the adhesion-promoting layer (for example with the use of higher-boiling solvents) or to increase the adhesive bond of the adhesion-promoting layer between the silicone and the PMMA prosthesis plastic an annealing at temperatures exceeding 30° C. can be performed as well.

In the direct relining method (chair-side) the prosthesis provided with the relining adhesive and the relining silicone is inserted into the mouth of the patient.

During the pot life of the relining silicone a functional impression is performed, i.e., the patient's mimic motions are transferred to the relining silicone. Once removed, the cured relining can rapidly be processed by cutting or milling.

The surface roughnesses created by the processing are sealed by the relining sealing lacquer of the invention in a layer thickness from 0.1 to 1000 $\mu$m, preferably from 0.1 to 200 $\mu$m.

Other favourable embodiments of the invention are specified in the claims.

Hereinafter the invention is further illustrated by examples.

1. Preparation of a Relining Adhesive

400 Parts of methyl methacrylate and 100 parts of α-methacryloxypropyl-ω-vinyltetramethyldisiloxane are added to 1.5 parts of dibenzoyl peroxide. The mixture is stirred at room temperature until the dibenzoyl peroxide is dissolved. Subsequently, 1.5 parts of N,N-dimethyltoluidine are added under a flow of argon. The obtained reaction solution is heated to 40° C. with stirring under a protective argon atmosphere. After termination of the reaction, e.g., after 40 min a weakly yellowish product is obtained.

2. Preparation of a Relining Adhesive in the Form of a Solution

5 Parts of the product prepared in example 1 are dissolved in 95 parts of dichloromethane. The obtained solution is an embodiment of the one-component relining adhesive of the invention.

3. Preparation of a Soft Relining Silicone a) Preparation of Component A

In a sealed kneader 82 parts of a vinyl-terminal polydimethylsiloxane having a viscosity of 10,000 mPa·s at 20° C.

are homogenized with 17 parts of a pyrogenically prepared, highly dispersed, hydrophilized silicic acid having a BET surface of 200 m$^2$/g, 1 part of a platinum catalyst dissolved in polydimethylsiloxane having a content of pure platinum of 1% for 1.5 h and subsequently degassed in the vacuum for 15 min.

A medium-flowing paste is obtained. The paste is a possible embodiment of component A of the soft relining silicone of the invention.

After a storage time at 23° C. of one month the viscosity and the reactivity of the paste were still within the range of required values.

b) Preparation of Component B

In a sealed kneader 68 parts of a vinyl-terminal polydimethylsiloxane having a viscosity of 10,000 mPa·s at 20° C. are homogenized with 7 parts of a 1:1 mixture of two polydimethylhydrogensiloxanes having SiH contents of 0.33 and 4.3 mmol/g, resp., 25 parts of a pyrogenically prepared, highly dispersed, hydrophilized silicic acid having a BET surface of 200 m$^2$/g for 1.5 h and subsequently degassed in the vacuum for 15 min.

A medium-flowing paste (DIN EN 24823) is obtained. The paste is a possible embodiment of component B of the relining silicone of the invention.

After a storage time at 23° C. of one month the viscosity and the reactivity of the paste were still within the range of required values.

c) Mixing Components A and B of the Relining Silicone

50 Parts of the component A described under 3a) and 50 parts of the component B described under 3b) are discharged from a cartridge and homogeneously mixed by a static mixer. At room temperature the product is processible for 1 min and at a temperature of 35° C. for additional 2 min, and it cures completely within 10 min after the beginning of mixing.

As a vulcanizate soft, highly elastic formed pieces are obtained which attain a tear strength of 502 N/cm$^2$ at an elongation of 718% in a tensile test (DIN 53455) performed after one week.

Contrary to the commercial products 2 and 3, the mechanical processability of the prepared vulcanizate using a rotating milling cutter (type: Meisinger HM72SX, speed: 25,000 rpm) is good. Even in thin layers fine structures can be prepared by milling without any erasing effect occurring or any larger silicone fragments being uncontrolledly torn out.

4. Preparation of a Soft Relining Silicone Having an Extremely High Tear Strength a) Preparation of Component A In a sealed kneader 69 parts of a vinyl-terminated poly-dimethylsiloxane having a viscosity of 1000 mPa·s at 20° C. are homogenized with 30 parts of a pyrogenically prepared, highly dispersed, hydrophilized silicic acid having a BET surface of 200 m$^2$/g, 1 part of a platinum catalyst dissolved in polydimethylsiloxane having a content of pure platinum of 1% for 1.5 h and subsequently degassed in the vacuum for 15 min.

A medium-flowing paste is obtained. The paste is a possible embodiment of component A of the soft relining silicone of the invention.

After a storage time at 23° C. of one month the viscosity and the reactivity of the paste were still within the range of required values.

b) Preparation of Component B

In a sealed kneader 50 parts of a vinyl-terminal polydimethylsiloxane having a viscosity of 1000 mPa·s at 20° C. are homogenized with 6 parts of a vinyl-terminal polydimethylsiloxane having a viscosity of 10,000 mPa·s at 20° C., 32 parts of a pyrogenically prepared, highly dispersed, hydrophilized silicic acid having a BET surface of 200 m$^2$/g, 1 part of a polydimethylsiloxane having terminal and side-chain vinyl groups and a viscosity of 5000 mPa·s at 20° C. and a vinyl content of 0.8 mmol/g, 1 part of a solid MQ silicone resin having a vinyl content of 0.7 mmol/g, with 10 parts of a 1:1 mixture of two polydimethylhydrogensiloxanes having SiH contents of 0.13 and 4.3 mmol/g, resp., for 1.5 h and subsequently degassed in the vacuum for 15 min.

A medium-flowing paste is obtained. The paste is a possible embodiment of component B of the relining silicone of the invention.

After a storage time at 23° C. of one month the viscosity and the reactivity of the paste were still within the range of required values.

c) Mixing Components A and B of the Relining Silicone

50 Parts of the component A described under 4a) and 50 parts of the component B described under 4b) are discharged from a cartridge and homogeneously mixed by a static mixer.

At room temperature the product is processible for 1 min and at a temperature of 35° C. for additional 2 min and it cures completely within 10 min after the beginning of mixing.

As a vulcanizate soft, highly tear resistant formed pieces are obtained which attain a tear strength of 670 N/cm$^2$ at an elongation of 120% in a tensile test (DIN 53455) performed after 24 h.

The mechanical processability is analogous to that of example 3c).

5. Preparation of a Hard Relining Silicone a) Preparation of Component A

In a sealed kneader 650 parts of a vinyl-terminated polydimethylsiloxane having a viscosity of 200 mPa·s at 20° C. are homogenized with 340 parts of a pyrogenically prepared, highly dispersed, hydrophilized silicic acid having a BET surface of 200 m$^2$/g and 10 parts of a platinum catalyst dissolved in polydimethylsiloxane having a content of-pure platinum of 1% for 1.5 h and subsequently degassed in the vacuum for 15 min.

A medium-flowing paste is obtained, said paste being a possible embodiment of component A of the hard relining silicone of the invention.

After a storage time at 23° C. of one month the viscosity and the reactivity of the paste were still within the range of required values.

b) Preparation of Component B

In a sealed kneader 400 parts of a vinyl-terminal polydimethylsiloxane having a viscosity of 200 mPa·s at 20° C. are homogenized with 400 parts of a mixture of two polydimethylhydrogensiloxanes having SiH contents of 0.33 and 6.9 mmol/g, resp., 300 parts of a pyrogenically prepared, highly dispersed, hydrophilized silicic acid having a BET surface of 200 m$^2$/g for 1.5 h and subsequently degassed in the vacuum for 15 min. A medium-flowing paste (DIN EN 24823) is obtained. The paste is a possible embodiment of component B of the relining silicone of the invention.

After a storage time at 23° C. of one month the viscosity and the reactivity of the paste were still within the range of required values.

c) Mixing Components A and B of the Relining Silicone

50 Parts of the component A described under 5a) and 50 parts of the component B described under 5b) are discharged from a cartridge and homogeneously mixed by a static mixer.

At room temperature the product is processible for 1 min and at a temperature of 35° C. for additional 2 min and it cures completely within 10 min after the beginning of mixing.

As a vulcanizate hard, viscoplastic formed pieces are obtained which attain a tear strength of 533 N/cm$^2$ at an elongation of 77% in a tensile test (DIN 53455) performed after one week.

The mechanical processability is analogous to that of example 3c).

6. Preparation of a Standard Dental Silicone Having a Medium-Flowing Consistency a) Preparation of Component A In a sealed kneader 20 parts of a vinyl-terminated polydimethylsiloxane having a viscosity of 1000 mPa·s and 20 parts of a vinyl-terminated polydimethylsiloxane having a viscosity of 10,000 mPa·s are homogenized with 3 parts of a pyrogenically prepared, highly dispersed, hydrophilized silicic acid having a BET surface of 200 m$^2$/g, 56 parts of a fine quartz powder and 1 part of a platinum catalyst dissolved in polydimethylsiloxane having a content of pure platinum of 1% for 1.5 h and subsequently degassed in the vacuum for 15 min.

A medium-flowing paste is obtained, said paste being component A of a standard dental substance.

b) Preparation of Component B

In a sealed kneader 20 parts of a vinyl-terminal polydimethylsiloxane having a viscosity of 10,000 mPa·s and 7 parts of a vinyl-terminal polydimethylsiloxane having a viscosity of 65,000 mPa·s are homogenized with 6 parts of a organohydrogenpolysiloxane having a SiH content of 2.3 mmol/g and a viscosity of 230 mPa·s and 3 parts of a pyrogenically prepared, highly dispersed, hydrophilized silicic acid having a BET surface of 200 m$^2$/g and 55 parts of a fine quartz powder for 1.5 h and subsequently degassed in the vacuum for 15 min.

A medium-flowing paste is obtained, said paste being component B of a standard dental substance.

c) Mixing Components A and B of the Standard Dental Silicone

50 Parts of the component A described under 6a) and 50 parts of the component B described under 6b) are homogeneously mixed by means of a mixing spatula on a mixing block. The product has a pot life of 1 min 30 s and cures within 6 min after the beginning of mixing As a vulcanizate a semirigid, moderately tear-resistant formed piece is obtained which attains a tear strength of 200 N/cm$^2$ at a rotation of 190% in a tensile test (DIN 53455) performed after a storage time of one week at room temperature.

7. Preparation of the Relining Sealing Lacquer a) Component A

In a laboratory planetary dissolver 60 parts of a vinyl-terminated polydimethylsiloxane having a viscosity of 200 mPa·s at 20° C., 15 parts of a solid MQ silicone resin having a vinyl content of 1.0 mmol/g and a viscosity of 2000 mPa·s at 20° C. dissolved in organopolysiloxane are homogenized with 15 parts of a pyrogenically prepared, highly dispersed, hydrophilized silicic acid having a BET surface of 200 m$^2$/g and one portion of a trimethylsiloxy-terminal polydimethylsiloxane having a viscosity of 50 mPa·s at 20° C. and 0.5 parts of a platinum catalyst dissolved in polydimethylsiloxane having a content of pure platinum of 1% for 1.5 h and subsequently degassed in the vacuum for 15 min.

b) Component B

In a laboratory planetary dissolver 35 parts of a vinyl-terminal polydimethylsiloxane having a viscosity of 200 mPa·s at 20° C., 20 parts of a solution of an MQ resin in α,ω-divinylpolydimethylsiloxane having a vinyl content of 1.0 mmol/g and a viscosity of 2000 mPa·s at 20° C., one portion of a trimethylsiloxy-terminal polydimethylsiloxane having a viscosity of 50 mPa·s at 20° C., 16 parts of a pyrogenically prepared, highly dispersed, hydrophilized silicic acid having a BET surface of 200 m$^2$/g, 18parts of an organohydrogenpolydimethylsiloxane having a SiH content of 7 mmol/g and 15 parts of an organohydrogenpolydimethylsiloxane having a SiH content of 0.33 mmol/g are homogenized for 1.5 h and subsequently degassed in the vacuum for 15 min.

A low-viscous paste having a viscosity of 3000 mPa·s is obtained, said paste being a possible embodiment of component B of the relining silicone sealing lacquer of the invention.

After a storage time at 23° C. of one month the viscosity and the reactivity of the paste were still within the range of required values.

c) Mixing Components A and B of the Relining Silicone Sealing Lacquer

50 Parts of the component A described under 7a) and 50 parts of the component B described under 7b) are discharged from a cartridge and homogeneously mixed by a static mixer.

At room temperature the product is processible for 2 min, i.e., it can be spread by a brush for 2 min and it cures completely within 8 min after the beginning of mixing at room temperature.

As a vulcanizate soft, elastic formed pieces are obtained which attain a tear strength of 115 N/cm$^2$ at an elongation of 144% in a tensile test (DIN 53455) performed after 48 h.

8. Adhesive Bond—PMMA—Adhesive of the Invention—Silicone of the Invention

Two test samples having dimensions of 40 mm×12.5 mm×5 mm (length×width×thickness) were prepared from a cold-curing prosthesis plastic (cold cured resin, hot cured resin, and injection-mould prosthesis plastic) according to the manufacturer's specification, grinded by abrasive paper (grain 240) and cleaned by blowing with compressed air.

The adhesive of item 2 and, for comparison, the adhesive of commercial product 2 is applied with a brush on both cleaned PMMA test samples and put aside for 1 min to ensure the complete evaporation of the solvent.

Subsequently, the relining silicone mixed according to item 3c) and, for comparison, the mixed relining silicone of commercial product 2 are applied on one surface of a PMMA test sample coated with the adhesive of item 2 and the adhesive of commercial product 2, resp. The second PMMA test sample is positioned with the adhesive-coated surface on the first test sample such that a square overlapping area of 1 cm$^2$ of both test samples is formed.

The assembly is loaded on the overlapping area with a weight of 500 g for 15 s and thereafter stored at 35° C. in a water bath for 15 min and subsequently stored at room temperature for 16 h. mechanical processing any separation of the relining silicone from the prosthesis plastic cannot be observed.

As the values of table 2b) reveal, the relining system of the invention (examples of items 2 and 3c) has stronger adhesive bonds as compared with commercial product 2 with all three prosthesis plastics.

9. Tests of the Adhesive Bond Between the Base Prosthesis Material and the Relining Silicone After Permanently Repeated Stress Reversals The test of permanently repeated stress reversals simulates the forces occurring during the wearing time of a prosthesis, e.g., chewing stresses.

According to Haraldson, Karlsson, and Carlsson (3 Oral Rehab 6, 41–48 (1979)) a wearer of a prosthesis applies a maximum force of 77 N at a "comfortable point". Estimating an upper limit of 100 N (which approximately corresponds to three times the normal chewing force) for this value and—with a one-sided stress on the prosthesis—a load-carrying area of 300 mm$^2$, there results a compressive stress of about 0.3 N/mm$^2$ the prosthesis or a relining material would be exposed to at the most. With a "soft" silicone (having a modulus of elasticity of about 1 N/mm$^2$) this corresponds to a compression $\epsilon$ of 30% which would have to be realized during the repeated stress reversal test. In order to detect the shear loading occurring in the practice as well, a shear of the same order of magnitude is applied on the test sample at the same time. Like in reality, said loads should be repeated loads (cycling between zero and a maximum) having a compressive stress amplitude of 0.3 N/mm$^2$ and consequently a shear stress amplitude of 0.1 N/mm$^2$ (corresponding to $\epsilon=0.3$ and $\gamma=0.3$).

BRIEF DESCRIPTION OF THE DRAWINGS

FIG. 1 illustrates the geometric changes of the test sample during the repeated stress, wherein the soft-remaining, heavily hatched plastic is positioned between two PMMA blocks under combined shear and compression loads. The dimensions are in mm.

The tests are performed simultaneously with three test samples in order to be able to examine a representative random sample in a minimum of time. A simulation of the oral environment is realized by spraying with water (37° C.). $10^6$ Load alterations correspond to a clinical operating time of from 500 to 1000 days. Employing the illustrated test sample variant, the quality of the bond PMMA/soft-remaining plastic is determined in the most elegant and sensitive way by a tensile test and evaluated in direct comparison with test samples stored in the water bath at 37° C. for 48 h.

The results from table 2c demonstrate that contrary to commercial products a decrease of the adhesive bond after $10^6$ load alterations does not occur due to the bond strength between the relining silicone of the invention (example 4.3.c) and the relining adhesive of the invention (example 2).

Table 3 illustrates the tear strength/the adhesive bond of the relining system of the invention under various storage conditions. The values prove that any significant decrease of the tear strength/the adhesive bond does not occur.

TABLE 1

Comparative Tests of Relining Silicones

| | Tear strength (N/cm$^2$)[1] | | | Elongation (%)[1] | | | Resistance to a manually implied discharging (N)[2] |
|---|---|---|---|---|---|---|---|
| | 1 week, RT | 2 weeks, 60° C. | 12 h, 100° C. | 1 week, RT | 1 week, 60° C. | 12 h, 100° C. | |
| Example 4.3 c) | 502 | 553 | 556 | 718 | 628 | 582 | 332 |
| Example 4.4 c) | 670 | 680 | 680 | 120 | 110 | 105 | 380 |
| Example 4.5 c) | 530 | 446 | 482 | 77 | 54 | 39 | 353 |
| Example 4.6 c) | 200 | — | — | 190 | — | — | — |
| Commercial product 1 (batch: 587) | 138 | 177 | 202 | 351 | 327 | 365 | 757 |
| Commercial product 2 (batch: 72123) | 250 | 242 | 300 | 711 | 545 | 586 | 730 |
| Commercial product 3 (batch: 01) | 210 | 146 | 171 | 651 | 420 | 402 | 396 |

[1] The tear strengths and elongations were tested on the universal test apparatus Z010 of the Zwick company in accordance with DIN 53455 (S2 dumbbells, test rate 50 mm/min)
[2] The resistance to a manually implied discharging is measured using a filled 48 ml cartridge having an attached static mixer in a compression test (test rate 50 mm/min) in the universal test apparatus Z010 of the Zwick company having a special holding device for cartridges.
[3] Commercial product 1: Tokuyama Soft Relining of Tokuyama Corp., Tokyo
Commercial product 2: Ufi-Gel C of the Voco company, Cuxhafen
Commercial product 3: Mollosil Plus of the Detax Company, Karlsruhe TABLE 2a Comparative tests of the adhesive bond between relining silicones and the relining adhesive

| | 15 min/35° C. | | 1 week/60° C. | | 12 h/100° C. water bath | |
|---|---|---|---|---|---|---|
| | Adhesive bond fracture stress N/cm$^2$ | Fracture pattern | Adhesive bond fracture stress N/cm$^2$ | Fracture pattern | Adhesive bond fracture stress N/cm$^2$ | Fracture pattern |
| Example 4.3 c) | 179 | 100% | 284 | 100% | 412 | 100 |
| Commercial product 1 (batch: 587) | 75 | 100% | 67 | 100% | 114 | 100 |
| Commercial product 2 (batch: 72123) | 114 | 60% | 109 | 100% | 141 | 70 |
| Commercial product 3 (batch: 01) | 101 | 80% | 132 | 100% | 233 | 90 |

TABLE 2b

Comparative tests of the adhesive bond between relining silicones and the relining adhesive of various prosthesis plastics (measurement after a storage time of 16 h at room temperature)

| | Cold cured resin | | Hot cured resin | | Injection-mould prosthesis plastic | |
|---|---|---|---|---|---|---|
| | Adhesive bond fracture stress N/cm² | Fracture pattern | Adhesive bond fracture stress N/cm² | Fracture pattern | Adhesive bond fracture stress N/cm² | Fracture pattern |
| Example 4.3 c) | 186 | 100 | 216 | 100 | 144 | 80 |
| Commercial product 2 (batch: 72123) | 103 | 100 | 99 | 50 | 111 | 40 |

Comparative tests of the adhesive bond between the relining silicone and the relining adhesive of various prosthesis plastics (measurement after a storage time of 16 h at room temperature)

| | Cold cured resin[1] | | Hot cured resin[2] | | Injection-mould prosthesis plastic[3] | |
|---|---|---|---|---|---|---|
| | Adhesive bond fracture stress N/cm² | Fracture pattern | Adhesive bond fracture stress N/cm² | Fracture pattern | Adhesive bond fracture stress N/cm² | Fracture pattern |
| Example 4.3 c) | 186 | 100 | 216 | 100 | 144 | 80 |
| Commercial product 2 (batch: 72123) | 103 | 100 | 99 | 50 | 111 | 40 |

[1] = Paladur, Kulzer
[2] = Paladon 65, Kulzer
[3] = SR Ivocap plus, Ivoclar

TABLE 3c

Stress test of the relining systems of examples 4.1 c) and 4.3 c)

| Storage | | Duration [weeks] | Fracture strength [N/cm²] of the composite part | Fracture pattern [%] | Fracture strength, S2 dumbbell [N/cm²] |
|---|---|---|---|---|---|
| Air[2] | | 5 | 224 | 100 | 483 |
| Water[3] | | 5 | 200 | 100 | 463 |
| Saliva[4] | | 6 | 229 | 100 | 529 |
| Coffee[5] | | 6 | 243 | 100 | 473 |
| Water saturated with cigarette smoke[6] | | 5 | 171 | 100 | 584 |
| Fernet Branca[7] | | 6 | 211 | 100 | 468 |
| Brandy[8] | | 6 | 194 | 100 | 434 |
| Cleaner | Helon[9] | 5 | 239 | 100 | 493 |
| | 2-Phasen[10] | 5 | 221 | 100 | 494 |
| | Corega Raucher[11] | 5 | 217 | 100 | 515 |
| | Express[12] | 5 | 216 | 100 | 508 |
| | Corega Bio[13] | 5 | 200 | 100 | 528 |
| Mouth-rinse Corega[14] | | 5 | 196 | 100 | 506 |
| Disinfectant | Perform[15] | 4 | 329 | 100 | 579 |
| | Stamm Z[16] | 4 | 320 | 100 | 532 |
| | Lyso P[17] | 4 | 301 | 100 | 532 |
| | Lyso d[18] | 4 | 274 | 100 | 565 |
| | Stamm D[19] | 4 | 281 | 100 | 521 |
| Temperature cycling, 50 times[20] | | 5 | 206 | 100 | 551 |

[1] The stress tests were performed with three test samples per series of tests, respectively, said test samples being prepared according to the process of example 4.8. The fracture strength was measured by a tensile test on a Z010 universal test apparatus of the company Zwick (test speed 10 mm/min). Subsequent to the determination of the fracture strength the fracture pattern is visually examined. A fracture pattern of 100% indicates the ideal case of a purely cohesive failure within the silicone. After the fracture 100% of both sides of the PMMA test samples are covered with silicone. The adhesive bond between the PMMA and the silicone is unchanged and completely maintained. A fracture pattern of 0% corresponds to an adhesive failure between the PMMA and the silicone. The silicone is unchanged. Fracture patterns between 0 and 100% indicate appropriate graduations of the evaluation.
[2] Standard operating environment: 23° C. and 50% of air humidity according to DIN 24823.
[3] The water was dyed with 0.1% of food dye. A dyeing of the relining silicone and the adhesive area could not be observed.
[4] 10% of hydroxyethyl starch (HES 200/0.5) in an isotonic NaCl solution of the Fresenius company; batch no. GC 1011; undiluted liquid.
[5] Eduscho Business Daytime; dosage: 60 g per 1 l of water; boiled at 100° C.
[6] Water, saturated with cigarette smoke (Marlboro company); batch no. 03111
[7] Gold Krone of the company Nordbrand Nordhausen GmbH; batch no. L340609; undiluted liquid
[8] Fernet Branca of the Fratelli Branca company; batch no. L5891; undiluted liquid

TABLE 3c-continued

Stress test of the relining systems of examples 4.1 c) and 4.3 c)

| Storage | Duration [weeks] | Fracture strength [N/cm²] of the composite part | Fracture pattern [%] | Fracture strength, S2 dumbbell [N/cm²] |
|---|---|---|---|---|

[9] Helon dental prosthesis cleaner of the company Dental Kosmetik GmbH High Dent, Dresden; batch no. 17063141; dosage: 3 g per 150 ml of water (2% solution); daily replacement of the solution
[10] Blend a dent 2-Phasen-Reiniger of the company Wick Pharma, Schwalbach; batch no. 62368; dosage: 1 tablet per 150 ml of water; daily replacement of the solution
[11] Corega Raucher Tabs of the Block Drug Company Inc., Ratingen; batch no. 6FO3A1; dosage: 1 tablet per 150 ml of water; daily replacement of the solution
[12] Blend a dent Express cleaning granulate of the company Wick Pharma, Schwalbach; batch no. 6145; dosage: 1 portion per 150 ml of water; daily replacement of the solution
[13] Corega Tabs Bio Formel of the Block Drug Company Inc., Ratingen; batch no. T 6132; dosage: 1 tablet per 150 ml of water; daily replacement of the solution
[14] Corega Mundspulung of the Block Drug Company Inc., Ratingen; batch no. 94627, undiluted liquid
[15] Perform of the company Kettenbach, Eschenburg; dosage: 40 g per 2 l of water (2%); daily replacement of the solution
[16] Stammopur Z of the company Stamm, Berlin, batch no. 961211; dosage: 5% solution in water; daily replacement of the solution
[17] Lysoform P of the company Dr. H. Rosemann GmbH; batch no. 101225; dosage: 6% solution in water; daily replacement of the solution
[18] Lysoform D of the company Dr. H. Rosemann GmbH; batch no. 021306; dosage: 2.5% solution in water; daily replacement of the solution
[19] Stammoform D of the company Stamm, Berlin, batch no. 1041269; dosage: 10 g per 500 ml of water (2%); daily replacement of the solution
[20] The test samples stored in water were exposed to a temperature cycling between +5° C. and +60° C. and +60° C. and +5° C. during five weeks. Impairments of the fracture stress or the fracture pattern could not be observed.

TABLE 4

Comparative tests of relining silicones - relining lacquers

| | Tear strength | Elongation | Adhesive bond to the silicone | Adhesive bond to the adhesive |
|---|---|---|---|---|
| Example 4.6 c) | 115 | 144 | 100% | 100% |
| Commercial product 1 (batch: 91121P) | 18 | 80 | [2] | [2] |
| Commercial product 2 (batch: 72091) | [2] | [2] | [2] | [2] |
| Commercial product 3 (batch: 970301/401) | [2] | [2] | [2] | [2] |

Tear strength and elongation were measured according to DIN 53504 using S 2 dumbbells afer 2 days.
The mechanical properties of commercial product 2 and commercial product 3 and partially of commercial product 1 are insufficient excluding the determination of the specifications.

What is claimed is:

1. A relining kit, characterized in that it includes a relining adhesive having the following composition:
   a) an adhesive component Z as a pure substance from 0 to 99% by weight;
   b) a copolymer having the adhesive component Z as a component from 0 to 99% by weight;
   c) a copolymer in admixture with the starting materials of the polymerization (adhesive component Z, monomers) from 0 to 99% by weight;
wherein the sum of the parts by weight of components a), b), and c) is at least 0.1% by weight and the mixture) of the copolymer with the starting materials of the polymerization, the adhesive component Z and the monomers is composed of the following components;
   the copolymer from 0.1 to 99.9% by weight
   the adhesive component Z from 0.1 to 99.9% by weight
   the monomers from 0.1 to 99.9% by weight
   the sum of all three components being 100%;
   d) catalysts for accelerating the formation of the adhesive bond to the silicone to be bonded from 0 to 10% by weight;
   e) a solvent from 1 to 99.99% by weight;
   f) colourants from 0 to 20% by weight;
   g) surfactants, emulsifiers, and stabilisers from 0 to 20% by weight;
   h) an organohydrogensiloxane from 0 to 40% by weight;
   i) an α,ω-divinylpolydialkylsiloxane from 0 to 40% by weight;
wherein
   Z has the following general formula:

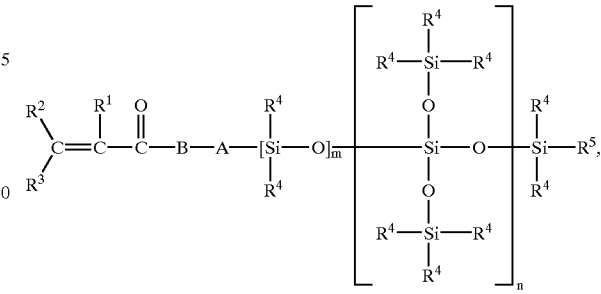

wherein n and m are integers in the range from 0 to 1000;

wherein R¹ is selected from the group consisting of hydrogen, halogen, alkyl, substituted alkyl and cyanide, R² is hydrogen, halogen, alkyl or substituted alkyl, R³ is a residue like R², B is O, S, NH, substituted nitrogen, PH or substituted phosphorus, A is a spacer of a straight-chain or branched hydrocarbon moiety with up to 30 C atoms which may also contain an aromatically unsaturated or a cycloaliphatic ring, R⁴ is selected from the group consisting of unsaturated groups, alkyl, aralkyl, halogeno-substituted alkyl and aryl groups, cyanoalkyl and cycloalkyl, wherein at least one of the residues R⁴ comprise a unsaturated group, R⁵ is equal to R⁴ or R⁶, and R⁶ is

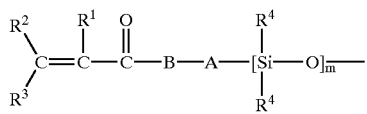

wherein R¹, R², R³, R⁴, A, B and m are as defined above, a two-component relining silicone having the following composition, in % by weight based on the weight of the composition:

a₁) from 0.1 to 80% by weight of organohydrogenpolysiloxanes or mixtures thereof having a SiH content from 2.0 to 15.0 mmol/g SiH, based on the polymer, and a viscosity from 10 to 10,0000 mPa·s at 20° C., a₂) from 0.1 to 80% by weight of organohydrogenpolysiloxanes or mixtures thereof having a SiH content from 0.03–2.0 mmol/g SiH, based on the polymer, and a viscosity from 10 to 70,0000 mPa·s at 20° C., b) from 1 to 90% by weight of organosiloxanes containing two vinyl groups within the molecule;

c) from 0.0001 to 1.0% by weight of catalysts, based on the content of the pure noble metal;

d) from 0 to 80% by weight of reinforcing fillers;

e) from 0 to 90% by weight of non-reinforcing fillers;

f) from 0 to 10% by weight of colourants;

g) from 0 to 50% by weight of moisture binders;

h) from 0 to 70% by weight of organopolysiloxanes containing more than two vinyl groups per molecule;

i) from 0 to 1.0% by weight of inhibitors;

j) from 0 to 90% by weight of solid or liquid MQ silicone resin;

k) from 0 to 80% by weight of a mixture of vinyl group-containing organopolysiloxanes and reinforcing fillers;

l) from 0 to 10% by weight of surfactants, emulsifiers, and stabilisers;

m) from 0 to 90% by weight of radiopaque substances;

n) from 0 to 20% by weight of H₂ absorbers/absorbers or substances reducing or eliminating the development of H₂;

o) from 0 to 50% by weight of plasticizers, neutral oils, and distributing oils; and, a two-component sealing lacquer contained within a cartridge wherein i) the two components chemically crosslink by a hydrosilylation reaction catalysed by noble metals, said component being an organopolysiloxane having a high SiH content from 2.0 to 15 mmol/g, based on the polymer, and an organohydrogenpolysiloxan having a low SiH content from 0.05 to 2 mmol/g, based on the polymer, the sealing lacquer having a viscosity from 25 to 10,000 mPa·s at 20° C., and ii) the ingredients of the two-component sealing lacquer corresponds to the ingredients of the relining silicone, wherein the relining adhesive, the two-component refining silicone, and the two-component sealing lacquer are provided for combining to prepare a relining.

2. The relining kit according to claim 1, characterized in that the monomers are methacrylates or acrylates.

3. The relining kit according to claim 1, characterized in that the monomers are alkyl methacrylate, cycloalkyl methacrylate, isoalkyl methacrylate, tetraethylene glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate, dodecanediol dimethacrylate, bisphenol A dimethacrylate, trimethylolpropane trtueacrylate, 2,2-bis-4 (3-methacryloxy-2-hydroxy)phenylpropane (bis-GMA) or reaction products from di and/or triiso-cyanates and OH group-containing methacrylates.

4. The relining kit according to claim 1, characterized in that the solvents are organic solvents or water.

5. The refining kit according to claim 4, characterized in that the solvents are aromatics, petroleum spirits, ethers, esters, alcohols, ketones, aldehydes, amines, carboxylic acids, halogenated solvents, or water or combinations there of.

6. A relining, characterized in that it is prepared by combining a relining adhesive having the following composition:
  a) an adhesive component Z as a pure substance from 0 to 99% by weight;
  b) a copolymer having the adhesive component Z as a component from 0 to 99% by weight;
  c) a copolymer in admixture with the starting materials of the polymerization (adhesive component Z, monomers) from 0 to 99% by weight;

wherein the sum of the parts by weight of components a), b), and c) is at least 0.01% by weight and the mixture c) of the copolymer with the starting materials of the polymerization, the adhesive component Z and the monomers is composed of the following components:

the copolymer from 0.1 to 99.9% by weight
  the adhesive component Z from 0.1 to 99.9% by weight
  the monomers from 0.1 to 99.9% by weight
  the sum of all three components being 100%;
  d) catalysts for accelerating the formation of the adhesive bond to the silicone to be bonded from 0 to 10% by weight;
  e) a solvent from 1 to 99.99% by weight;
  f) colourants from 0 to 20% by weight;
  g) surfactants, emulsifiers, and stabilisers from 0 to 20% by weight;
  h) an organohydrogensiloxane from 0 to 40% by weight;
  i) an α,ω-divinylpolydialkylsiloxane from 0 to 40% by weight;

wherein
Z has the following general formula:

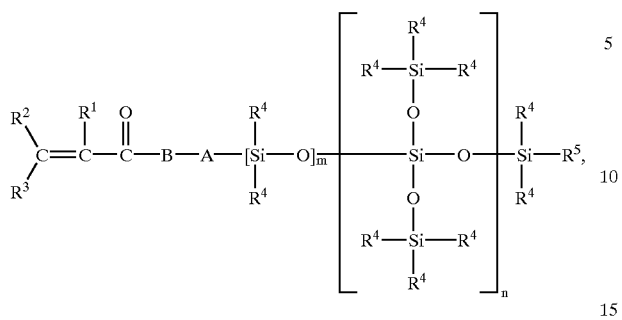

wherein n and m are integers in the range from 0 to 1000;

wherein $R^1$ is selected from the group consisting of hydrogen, halogen, alkyl, substituted alkyl and cyanide, $R^2$ is hydrogen, halogen, alkyl, or substituted alkyl, $R_3$ residue like $R^2$, B is O, S, NH, substituted nitrogen, PH or substituted phosphorus A is a spacer of a straight-chain or branched hydrocarbon moiety with up to 30 C atoms which may also contain an aromatically unsaturated or a cycloaliphatic ring, $R^4$ is selected from the group consisting of unsaturated groups, alkyl, aryl, aralkyl, halogeno-substituted alkyl and aryl groups, cyanoalkyl and cycloalkyl wherein at least one of the residues $R^4$ comprise a unsaturated group, $R^5$ is equal or $R^4$ or $R^6$, and $R^6$ is

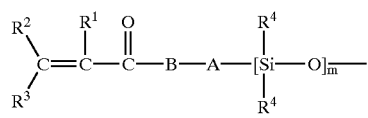

wherein $R^1$, $R^2$, $R^3$, $R^4$, A, B and m are as defined above, a two-component relining silicone having the following composition, in % by weight based on the weight of the composition:

$a_1$) from 0.1 to 80% by weight of organohydrogenpolysiloxanes or mixtures thereof having a SiH content from 2.0 to 15.0 mmol/g SiH, based on the polymer, and a viscosity from 10 to 10,0000 mPa·s at 20° C., $a_2$) from 0.1 to 80% by weight of organohydrogenpolysiloxanes or mixtures thereof having a SiH content from 0.03–2.0 mmol/g SiH, based on the polymer, and a viscosity from 10 to 70,0000 mPa·s at 20° C., b) from 1 to 90% by weight of organosiloxanes containing two vinyl groups within the molecule;

c) from 0.0001 to 1.0% by weight of catalysts, based on the content of the pure noble metal;

d) from 0 to 80% by weight of reinforcing fillers;

e) from 0 to 90% by weight of non-reinforcing fillers;

t) from 0 to 10% by weight of colourants;

g) from 0 to 50% by weight of moisture binders;

h) from 0 to 70% by weight of organopolysiloxanes containing more than two vinyl groups per molecule;

i) from 0 to 1.0% by weight of inhibitors;

j) from 0 to 90% by weight of solid or liquid MQ silicone resin;

k) from 0 to 80% by weight of a mixture of vinyl group-containing organopolysiloxanes and reinforcing fillers;

l) from 0 to 10% by weight of surfactants, emulsifiers, and stabilisers;

m) from 0 to 90% by weight of radiopaque substances;

n) from 0 to 20% by weight of $H_2$ absorbers/absorbers or substances reducing or eliminating the development of $H_2$;

o) from 0 to 50% by weight of plasticizers, neutral oils, and distributing oils; and, a two-component sealing lacquer contained within a cartridge wherein i) the two components chemically crosslink by a hydrosilylation reaction catalysed by noble metals, said component being an organopolysiloxane having a high SiH content from 2.0 to 15 mmol/g, based on the polymer, and an organohydrogenpolysiloxan having a low SiH content from 0.05 to 2 mmol/g, based on the polymer, the sealing lacquer having a viscosity from 25 to 10,000 mPa·s at 20° C., and ii) the ingredients of the two-component sealing lacquer corresponds to the ingredients of the relining silicone.

7. The relining according to claim 6, characterized in that the monomers are methacrylates or acrylates.

8. The relining according to claim 6, characterized in that the monomers are alkyl methacrylate, cycloalkyl methacrylate, isoalkyl methacrylate, tetraethylene, glycol dimethacrylate, triethylene glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate, dodecanediol dimethacrylate, bisphenol A dimethacrylate, trimethylolpropane trimethacrylate, 2,2-bis-4(3-methacryloxy-2-hydroxy)phenylpropane (bis-GMA) or reaction products from di and/or triiso-cyanates and OH group-containing methacrylates.

9. The relining according to claim 6, characterized in tat the solvents are organic solvents or water.

10. The relining according to claims 9, characterized in that the solvents are aromatics, petroleum spirits, ethers, esters, alcohols, ketones, aldehydes, amines, carboxylic acids, halogenated solvents, or water or combinations there of.

* * * * *